United States Patent [19]

Posthuma et al.

[11] Patent Number: 5,486,542
[45] Date of Patent: Jan. 23, 1996

[54] PROCESS FOR THE DISTILLATION OF FISHER-TROPSCH PRODUCTS

[75] Inventors: Sytze A. Posthuma; Hermanus M. H. Wechem; Hendrikus Heetveld, all of The Hague, Netherlands

[73] Assignee: Shell Oil Company, Houston, Tex.

[21] Appl. No.: 486,157

[22] Filed: Jun. 7, 1995

Related U.S. Application Data

[63] Continuation of Ser. No. 188,495, Jan. 28, 1994, abandoned.

[51] Int. Cl.$^6$ .................................................. C07C 27/00
[52] U.S. Cl. .......................... 518/700; 518/715; 518/726
[58] Field of Search ..................................... 518/700, 715, 518/726, 728

[56] References Cited

U.S. PATENT DOCUMENTS 5,032,249  7/1991  Jones et al. ................................ 208/24

FOREIGN PATENT DOCUMENTS 428223     5/1991  European Pat. Off. .
579330A1   1/1994  European Pat. Off. .

OTHER PUBLICATIONS

"The Shell Middle Distillate Synthesis" Plant at Bintulu, published approximately May 1991.

*Primary Examiner*—Werren B. Lone

[57] ABSTRACT

A process for the distillation of a hydrocarbon mixture, which mixture has been prepared by a Fischer-Tropsch synthesis, comprises supplying the hydrocarbon mixture to a wiped film evaporator and recovering a first fraction having a low boiling point range and a narrow melting point range as the light product from the evaporator and recovering a second fraction having a high boiling point range and a wider melting point range as the heavy product of the evaporator. The process is particularly suitable for the distillation of hydrocarbons having a carbon number of $C_{20}$ or greater.

9 Claims, No Drawings

PROCESS FOR THE DISTILLATION OF FISHER-TROPSCH PRODUCTS

This is a continuation of application Ser. No. 08/188,495, filed Jan. 28, 1994 abandoned.

FIELD OF THE INVENTION

The present invention relates to a process for the distillation of waxes, in particular hydrocarbon waxes, such as paraffin waxes produced by a Fischer-Tropsch synthesis.

BACKGROUND OF THE INVENTION

It is well known in the art that hydrocarbons may be prepared by means of the Fischer-Tropsch synthesis, in which a mixture of carbon monoxide and hydrogen is contacted at elevated temperature and pressure with a suitable catalyst. Recently, it has been found that certain catalysts active in the Fischer-Tropsch synthesis are highly selective in the preparation of hydrocarbons having high molecular weights, in particular paraffinic hydrocarbons. Fischer-Tropsch catalysts comprising cobalt as the catalytically active metal have been found to be particularly selective in the preparation of the aforementioned paraffinic hydrocarbons.

In the preparation of commercial products from the hydrocarbon effluent of the Fischer-Tropsch synthesis, it is most convenient to separate and refine the components of the effluent by applying distillation. The lower molecular weight components of the hydrocarbon effluent may be separated and refined by means of conventional distillation techniques operated at atmospheric or super-atmospheric pressures. However, the higher molecular weight components of the hydrocarbon effluent may be subject to thermal degradation at the high temperatures encountered in conventional atmospheric distillation operations. To avoid such degradation occurring, it is necessary to apply vacuum distillation techniques in the separation and refining of these higher molecular weight components.

A variety of vacuum distillation techniques and apparatus are known for separating and refining thermally sensitive materials, for example the operation under vacuum of conventional distillation columns as practiced in the conventional refining of crude oil. In addition, a number of specific vacuum distillation techniques have been developed, for example the short-path vacuum distillation techniques.

More recently, the use of a specific distillation apparatus, namely the wiped film evaporator, has been proposed for use in refining the thermally sensitive, high molecular weight hydrocarbons recovered from conventional crude oil refining operations. Thus, U.S. Pat. No. 5,032,249 discloses a process in which a petroleum wax, in particular a heavy intermediate petroleum wax, is separated into two fractions in a wiped film evaporator to provide a lower boiling fraction having a narrow melting range and a higher boiling fraction having a wider melting range.

It has now been found that wiped film evaporators may be advantageously applied in the separation and refining of the hydrocarbon product of a Fischer-Tropsch synthesis, in particular the higher molecular weight hydrocarbon components of the product.

SUMMARY OF THE INVENTION

The present invention therefore provides a process for the distillation of a hydrocarbon mixture, which mixture has been prepared by a Fischer-Tropsch synthesis, which process comprises supplying the hydrocarbon mixture to a wiped film evaporator and recovering a first fraction having a low boiling point range and a narrow melting point range as the light product from the evaporator and recovering a second fraction having a high boiling point range and a wider melting point range as the heavy product of the evaporator.

DESCRIPTION OF THE PREFERRED EMBODIMENTS

The process of the present invention provides the advantage that the hydrocarbon products of the Fischer-Tropsch synthesis may be separated and refined without substantial degradation of the product occurring, the products of which require little or no finishing treatment to meet the standards required of commercial hydrocarbon products. In particular, it has been found possible to prepare hydrocarbon wax products achieving excellent standards of color and odor. The hydrocarbon mixture for use as feed for the process of the present invention is prepared by means of the Fischer-Tropsch synthesis. In the Fischer-Tropsch synthesis, a mixture of carbon monoxide and hydrogen is contacted with a suitable synthesis catalyst at elevated temperature and pressures. Typical operating conditions for the synthesis are temperatures in the range of from about 125° C. to about 350° C., preferably from about 175° C. to about 250° C., and a pressure in the range of from about 5 to about 100 bar, preferable from about 10 to about 50 bar.

Suitable catalyst compositions for use in the Fischer-Tropsch synthesis are well known in the art. Catalytically active metals for use in the Fischer-Tropsch catalysts are typically selected from Group VIII of the Periodic Table of the Elements. In particular, metals selected from iron, cobalt, nickel and ruthenium have been found to be particularly suitable for preparing high molecular weight hydrocarbons. Cobalt-containing catalysts have been found to be especially suitable for use in the preparation of high molecular weight paraffinic hydrocarbons in high yields.

The catalytically active metal is preferably supported on a porous carrier. The porous carrier may be selected from any of the suitable refractory metal oxides or silicates or combinations thereof known in the art. Particular examples of preferred porous carriers include silica, alumina, titania and mixtures thereof. Silica is a particularly preferred carrier material.

The amount of catalytically active metal on the carrier is preferably in the range of from about 3 to about 10 parts by weight per 100 parts by weight of carrier material, more preferable from about 10 to about 80 parts by weight.

Catalysts for use in the Fischer-Tropsch synthesis may also comprise one or more co-catalysts or promoters. Suitable promoters include oxides of metals selected from Groups IIA, IIIB, IVB, VB and VIB of the Periodic Table of the Elements, or the actinides or the lanthanides. Oxides of metals from Group IVB of the Periodic Table, in particular titanium and zirconium, are preferred. Suitable metal promoters include metals of Group VIII of the Periodic Table, with platinum and palladium being preferred. The amount of promoter present in the catalyst is in the order of from about 0.1 to about 150 parts by weight per 100 parts by weight of the carrier material.

Processes for preparing suitable Fischer-Tropsch catalysts are known in the art, for example as described in European Patent Applications Publication Nos. EP 0,104,672, EP 0,110,449, EP 0,127,220, EP 0,167,215, EP 0,180,269, EP 0,221,598 and EP 0,428,223.

The hydrocarbon mixture produced by the Fischer-Tropsch synthesis comprises a wide range of hydrocarbon components having a wide range of molecular weights. The lower molecular weight or lighter components may be removed from the mixture by conventional distillation techniques prior to the mixture being used as feed in the process of the present invention. The process of the present invention has been found to be particularly suitable for the separation and refining of Fischer-Tropsch hydrocarbon products having a carbon number of $C_{20}$ and above. The process has been found to be especially suited to the refining of substantially paraffinic hydrocarbons having carbon numbers in this range. It is to be noted that paraffinic hydrocarbons having carbon numbers of $C_{20}$ or greater and produced by the Fischer-Tropsch synthesis are present as solids under conditions of ambient temperature and pressure.

The wiped film evaporators (also referred to as agitated thin-film evaporators) for use in distillation process of the present invention are known in the art and are available commercially. In this respect, for a general discussion of the principle of operation of these evaporators reference is made to "Agitated Thin-Film Evaporators: A Three Part Report", Parts 1 to 3; A. B. Mutzenburg, N. Parker and R. Fischer; Chemical Engineering, Sep. 13, 1965.

Typically, wiped film evaporators comprise a generally cylindrical evaporating vessel. The vessel may be either vertical or horizontal, with vertically arranged vessels being preferred. The evaporator further comprises a rotor mounted within the cylindrical evaporating vessel and provided with a number of wiper blades. A motor is provided to drive the rotor. The rotor is arranged within the cylindrical evaporating vessel so that, upon rotation by the motor, the wiper blades are caused to move over the inner surface of the cylindrical vessel. The wiper blades may contact the inner surface of the cylindrical vessel. Alternatively, a gap or clearance may be left between the tips of the wiper blades and the inner surface of the cylindrical vessel.

In operation, the hydrocarbon mixture to be separated or refined is fed, supplied or subjected to the evaporator and forms a thin film over the inner surface of the cylindrical vessel. The film is heated, typically by means of indirect heat exchange with a heating medium through the wall of the cylindrical vessel, for example steam. The action of the wiper blades in passing over the surface is to agitate the film of hydrocarbons, resulting in turbulence in the film, which in turn improves heat and mass transfer. In addition, the wiper blades ensure an even distribution of the hydrocarbons over the inner surface of the vessel and prevent channelling of the liquid as it passes across the surface. Under the action of the wiper blades and the heating, the lighter components of the hydrocarbon mixture are caused to evaporate.

The light product is removed from the evaporator as a vapor and is subsequently condensed. Condensing is conveniently effected by indirect heat exchange with a cooling medium, for example water. The condenser may be separate from the evaporator vessel or may be located within the vessel. In the latter case, the vessel will comprise a first evaporating section in which the rotor and wiper blades are arranged and a second condensing section in which the condenser is housed. If desired, a separating section may be disposed between the evaporating section and the condensing section to allow removal of any liquid droplets entrained in the vapor prior to condensing.

The heavy product is removed from the evaporator as a liquid leaving the inner surface of the cylindrical vessel. The wiped film evaporator is operated under a vacuum. Suitable pumps for the generation and maintenance of the vacuum are well known in the art. Typical examples of suitable pumps include steam ejector pumps and diffusion vacuum pumps.

During the operation of the process of the present invention, the hydrocarbon mixture to be separated is first heated to a temperature sufficient to soften and melt the mixture, if necessary, and to reduce the viscosity of the mixture, thereby allowing it flow. The hydrocarbon mixture is then introduced into the evaporator to form a thin film on the inner surface of the cylindrical evaporator vessel. The operating pressures for the wiped film evaporators will vary according to the precise hydrocarbon feedstock. Typical operating pressures are in the range of from about 0.02 to about 10 millibar absolute (mbara), more preferable from about 0.05 to about 7.5 mbara. Operating temperatures for the wiped film evaporator will also depend upon the particular feedstock being processed. Typically, operating temperatures of the wiped film evaporator will be in the range of from about 100° C. to about 350° C., more preferably in the range of from about 150° C. to about 300° C. The residence time of the wax within the evaporator is relatively very low, compared with that of a conventional vacuum distillation apparatus. Typical residence times range from about 20 seconds to about 5 minutes, depending upon the feedstock and the design of evaporator being employed. It is important, however, that the operating temperature is not so high as to lead to a substantial degree of thermal degradation or cracking of the hydrocarbon mixture being processed at the particular residence time and that the operating conditions of temperature and pressure are selected to ensure that such high temperatures are not required.

The process of the present invention is applied in the separation of the hydrocarbon mixture feed into a light fraction having a narrow melting point range and a heavy fraction having a wider melting point range. Generally, a given fraction or grade of hydrocarbon will comprise hydrocarbons having a range of melting points and boiling points. Accordingly, it is usual to assign a melting point range to a fraction, which range extends from the melting point of the lightest or lowest melting component to the heaviest or highest melting component. Suitable methods for determining the melting point range of a hydrocarbon fraction are well known in the art and described, for example, in The Chemistry and Technology of Waxes by A. H. Warth, Second Edition, Reinhold Publishing Corporation, at pages 602 to 605.

The process of the present invention may be used to distill hydrocarbon mixtures prepared by Fischer-Tropsch synthesis and comprising compounds having carbon numbers ranging, for example, from $C_{18}$ to $C_{40}$ and even higher. Such a hydrocarbon mixture substantially consisting of paraffinic hydrocarbons and comprising $C_{18}$ to $C_{40+}$ compounds typically has a melting point range of from about 28° C. to in excess of 83° C. A typical light product from the wiped film evaporator may comprise compounds in the range of from $C_{18}$ to $C_{20}$, having a melting point range of from about 28° C. to about 38° C. and a boiling point range of from about 315° C. to about 345° C. (under atmospheric conditions of pressure).

In another typical process scenario, a hydrocarbon feed substantially consisting of paraffinic hydrocarbons and comprising compounds having carbon numbers in the range of from $C_{21}$ to $C_{40}$ and higher, having a melting point range of from about 40° C. to in excess of 83° C. and a boiling point range of from about 355° C. to in excess of 390° C. (under atmospheric pressure), may be distilled in a wiped film evaporator to yield a light product comprising compounds in the range of from $C_{21}$ to $C_{27}$, having a melting point range of from about 40° C. to about 60° C. and a boiling point range of from about 355° C. to 442° C. (under atmospheric pressure). Other light fractions having different ranges of melting points and boiling points may also be prepared.

The hydrocarbon mixture may be refined into a range of fractions in a number of stages, with one or more wiped film evaporators being employed in each stage.

The hydrocarbon products of the process of this invention may be subjected to conventional finishing processes known in the art to yield a commercially acceptable material. Such finishing processes include mild hydrotreating or hydrofinishing. Hydrofinishing processes remove any oxygenates, olefins or aromatic hydrocarbons which may be present in the hydrocarbon fractions leaving the wiped film evaporator. Suitable hydrofinishing processes, in particular catalytic hydrofinishing processes, are well known in the art. However, it has been found that the process of the present invention allows hydrocarbon mixtures prepared by Fischer-Tropsch synthesis processes to be distilled into the required fractions or grades without significant degradation or cracking of the feed occurring. This in turn results in significantly less or even no finishing treatments being needed to meet the requirements of, for example, color and odor of the finished hydrocarbon fraction.

The process of the present invention will be further described, by way of illustration only, in the following example.

EXAMPLE

Hydrocarbon Preparation

A hydrocarbon mixture was prepared by means of the Fischer-Tropsch synthesis using the following method:

A cobalt/zirconium/silica catalyst was prepared following the procedure described in European Patent Application publication No. 0, 428,223. The catalyst was loaded into a reaction vessel and reduced by contacting the catalyst with a mixture of hydrogen and nitrogen at a temperature of 250° C., a pressure of 5 bar and a gas hourly space velocity of from 500 to 600 Nl/l/h. The activated catalyst was then contacted with a mixture of carbon monoxide and hydrogen having a hydrogen/carbon monoxide ratio of 1.1 at a gas inlet pressure of from 37 to 39 bar, a temperature of from 210° to 220° C. and a gas hourly space velocity of from 1110 to 1130 Nl/l/h. The product of the reaction was a mixture of substantially paraffinic hydrocarbons.

The hydrocarbon fraction was subjected to a conventional distillation to remove the $C_{20}$-components, leaving a $C_{21}+$ hydrocarbon mixture.

Distillation of Hydrocarbon Mixture

The $C_2+$ hydrocarbon mixture produced as hereinbefore described was fed to a vertical wiped film evaporator of the SAMVAC type. The wiped film evaporator was operated at a temperature of between 190° and 195° C. and a pressure of 0.1 mbara. The vapor leaving the wiped film evaporator was collected and condensed to yield a light hydrocarbon fraction. The liquid leaving the wiped film evaporator was collected as a heavy fraction. The carbon number distribution of the light and heavy fractions recovered is given in Table 1.

TABLE 1

|  | Light Fraction (wt %) | Heavy Fraction (wt %) |
|---|---|---|
| $C_{20}-$ | 0.2 | 0.0 |
| $C_{21}$ to $C_{27}$ | 67.3 | 1.7 |
| $C_{28}$ to $C_{40}$ | 32.5 | 39.2 |
| $C_{40}+$ | trace | 59.1 |

The light hydrocarbon fraction recovered had a Saybolt color of greater than +30, a penetration value (at 25° C.) of 34 and a melting point of 53° C. The light hydrocarbon fraction did not require further finishing treatment.

We claim:

1. A process for the distillation of a hydrocarbon mixture, which mixture has been prepared by a Fischer-Tropsch synthesis, which process comprises supplying the hydrocarbon mixture to a wiped film evaporator and recovering a first fraction having a low boiling point range and a narrow melting point range as the light product from the evaporator and recovering a second fraction having a high boiling point range and a wider melting point range as the heavy product of the evaporator.

2. The process according to claim 1, characterized in that the hydrocarbon mixture consists of hydrocarbons having a carbon number in the range of from $C_{20}$ and above.

3. The process according to claim 2, characterized in that the hydrocarbon mixture consists of paraffinic hydrocarbons.

4. The process according to claim 1, characterized in that the hydrocarbon mixture has been prepared by a Fischer-Tropsch synthesis comprising contacting hydrogen and carbon monoxide with a cobalt-containing catalyst.

5. The process according to claim 1, characterized in that the wiped film evaporator is operated at a temperature in the range of from about 150° C. to about 300° C.

6. The process according to claim 1, characterized in that the wiped film evaporator is operated at a pressure in the range of from about 0.02 to about 10 mbara.

7. The process according to claim 6, characterized in that the wiped film evaporator is operated to allow a residence time of the hydrocarbon mixture in the evaporator of from about 20 seconds to about 5 minutes.

8. The process according to claim 1, wherein said process further comprises subjecting a hydrocarbon product recovered from the wiped film to a hydrofinishing step.

9. The process according to claim 8, characterized in that the heavy product recovered from the wiped film evaporator is subjected to a hydrofinishing step.

\* \* \* \* \*